United States Patent [19]

Kitatani et al.

[11] 4,427,768
[45] Jan. 24, 1984

[54] METHOD OF HARDENING GELATIN

[75] Inventors: Katuji Kitatani; Hidefumi Sera; Atsuaki Arai; Masasi Ogawa; Kunio Ishigaki, all of Minami-ashigara; Haruo Ogura, Matsudo, all of Japan

[73] Assignee: Fuji Photo Film Co., Ltd., Kanagawa, Japan

[21] Appl. No.: 394,988

[22] Filed: Jul. 2, 1982

Related U.S. Application Data

[62] Division of Ser. No. 188,391, Sep. 18, 1980, abandoned.

[30] Foreign Application Priority Data

Sep. 18, 1979 [JP] Japan ................................ 54-119480

[51] Int. Cl.$^3$ ............................................. G03C 1/30
[52] U.S. Cl. ...................................... 430/623; 430/621
[58] Field of Search ................................ 430/621, 623

[56] References Cited
U.S. PATENT DOCUMENTS 4,052,373 10/1977 Sera et al. ........................... 430/621
4,066,636 1/1978 Sera et al. ........................... 430/623
4,111,926 9/1978 Sera et al. ........................... 430/623

*Primary Examiner*—Mary F. Downey
*Attorney, Agent, or Firm*—Sughrue, Mion, Zinn, Macpeak & Seas

[57] ABSTRACT

A method of hardening gelatin is described comprising treating gelatin with a compound of the formula (I)

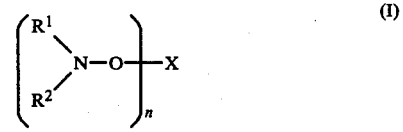

wherein
$R^1$ and $R^2$ can each represent a monovalent group including a carbon atom or a nitrogen atom forming a bond together with the nitrogen atom N forming an acid ester in the formula (I); or $R^1$ and $R^2$ together can form a heterocyclic ring together with said nitrogen atom N, and
n is 1 or 2; and
when n is 1, X is

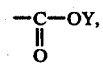

and Y is an alkyl group, an aryl group or an aralkyl group; and when n is 2, X is

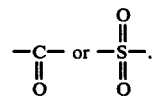

5 Claims, No Drawings

METHOD OF HARDENING GELATIN

This is a division of application Ser. No. 188,391, filed Sept. 18, 1980, now abandoned.

BACKGROUND OF THE INVENTION

1. Field of the Invention

This invention relates to a method of hardening gelatin using an improved hardening agent and particularly to a method of hardening gelatin for silver halide photographic light-sensitive materials.

2. Description of the Prior Art

Gelatin has been used as a binder for many kinds of photographic light-sensitive materials. For example, gelatin has been used as a main component for silver halide light-sensitive emulsion layers, emulsion protective layers, filter layers, intermediate layers, antihalation layers, backing layers, subbing layers of film bases or baryta layers, and so forth.

These light-sensitive materials containing the gelatin are processed with various kinds of aqueous solutions, each with a different pH or with a different temperature. The properties of layers containing a gelatin which is not processed with a hardening agent depend mainly upon the properties of the gelatin used, and such layers typically have poor water resistance and low mechanical strength due to excessive swelling in the aqueous solutions. In extreme cases, the gelatin layers sometimes dissolve off into the solutions when aqueous solutions at a temperature higher than about 30° C. or highly alkaline aqueous solutions are used. This characteristic of dissolving under such conditions is a fatal defect for layers in photographic light-sensitive materials.

However, a number of compounds are known to be effective for hardening gelatin to improve the water resistant properties, heat resistant properties and scratch resistant properties of gelatin layers.

These compounds are known as "hardening agents" in the production of photographic light-sensitive materials. For example, known gelatin hardening agents include aldehyde compounds such as formaldehyde or glutaraldehyde, reactive halogen containing compounds as described in U.S. Pat. No. 3,288,775, et al., compounds having ethylenically unsaturated reactive bonds as described in U.S. Pat. No. 3,635,718, et al., aziridine compounds as described in U.S. Pat. No. 3,017,280, epoxy compounds as described in U.S. Pat. No. 3,091,537, halocarboxyaldehydes such as mucochloric acid, dioxanes such as dihydroxydioxane or dichlorodioxane, and inorganic hardening agents, such as chromium alum or zirconium sulfate, and so forth.

However, all of these known compounds have some disadvantages. Particularly, some have an insufficient hardening function when used for photographic light-sensitive materials, some cause undesirable changes to occur in image quality over a period of time, because of a hardening function called "post-hardening" which occurs due to a slow hardening reaction with gelatin, some compounds adversely influence the properties of the photographic light-sensitive materials (particularly increasing fogging and reducing sensitivity, etc.), some lose their hardening ability when certain photographic additives are present at the same time, or interfere with the functions of these other photographic additives (for example, couplers for color light-sensitive materials), some are difficult to synthesize in large quantities, and some have poor storability because they are unstable.

It has previously been proposed to use a post-hardening free hardener (that is, a hardener that can be used without the occurrence of the post-hardening phenomenon; also, as used herein the term "hardener" refers to a composition comprising a "hardening agent" compound, either alone or with other substances) comprising a compound having at least two N-acyloxysuccinimide groups in the molecule (Japanese Patent Publication No. 22089/78) or a compound having an N-sulfonyloxysuccinimide group (German Patent Application (OLS) No. 2,704,276). Such a hardener causes very rapid hardening of gelatin and substantially eliminates the possibility of post-hardening. The hardener is also free from such undesired effects as increased fogging and reduced sensitivity (caused by either the hardener itself or by a reaction by product thereof). Furthermore, it does not interact with other photographic additives, such as a coupler for color sensitive materials, to either interfere with the function of these additives or lose its hardening ability. Unfortunately, most of these otherwise excellent hardeners are low in water solubility, and require a special organic solvent for incorporation into a photographic emulsion or a photographic emulsion layer.

SUMMARY OF THE INVENTION

It has now been found that a compound of the formula (I) below has good affinity for water and functions as a hardener having the desirable characteristics described above.

Therefore, one object of this invention is to provide a method of hardening gelatin using a novel gelatin hardener.

Another object of this invention is to provide a quick-dry gelatin hardener capable of producing a photographic light-sensitive material having stable properties; particularly, a low swelling rate, a small degree of swelling of the gelatin-containing layer and very small variations in sensitivity and color balance with the lapse of time, as well as provide a method of hardening gelatin using such hardener.

A further object of this invention is to provide a novel gelatin hardening agent which produces gelatin with excellent water resistant, heat resistant and scratch resistant properties without adversely affecting the other properties of photographic light-sensitive materials.

Still another object of this invention is to provide a gelatin hardener which has high affinity for water and needs no special organic solvent for incorporation into a photographic emulsion or other hydrophilic colloidal solutions.

These objects of this invention are attained by hardening gelatin with a compound of the formula (I) below:

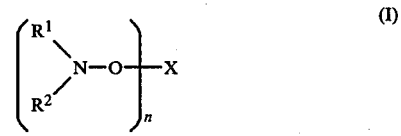

wherein
$R^1$ and $R^2$ can each represent a monovalent group including a carbon atom or a nitrogen atom forming a bond together with the nitrogen atom N forming an acid ester in the formula (I); or $R^1$ and $R^2$ together can form a heterocyclic ring together with said nitrogen atom N, and n is 1 or 2; and
when n is 1, X is

and Y is an alkyl group, aryl group or aralkyl group; and when n is 2, X is

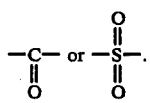

DETAILED DESCRIPTION OF THE INVENTION

The acid ester in the above formula (I) is a carboxylic acid ester or a sulfonic acid ester. When Y is an alkyl group, it preferably has from 1 to 8 carbon atoms; when Y is an aryl group, it preferably has from 6 to 12 carbon atoms; and when Y is an aralkyl group, it preferably has from 7 to 13 carbon atoms.

$R^1$ and $R^2$ preferably, when monovalent groups, contain a total of 4 or 5 carbon atoms, or, when $R^1$ and $R^2$ together form a heterocyclic ring which is preferably a 5- or 6-membered ring; $R^1$ and $R^2$ most preferably represent acyl groups or together form a 5- or 6-membered heterocyclic ring.

Examples of

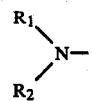

are 1-pyrrolidinyl group, 1-piperidinyl group, morpholino group, 2-isoindolinyl group, 1H-indazol-1-yl group, 4-oxo-3,4-dihydro-3-quinazolinyl group, 4-oxo-3,4-dihydro-1,2,3-benzotriazin-3-yl group, 1-pyrazolyl group, 1,2,3-benzotriazol-1-yl group, 1,2,3-naphthotriazol-1-yl group, phthalimide group, $\Delta^1$-tetrahydrophthalimide group, cyclohexane-1,2-dicarboxyimide group, 5-norbornene-2,3-dicarboxyimide group, succinimide group, maleimide group, glutarimide group, N,N-diacetylamino group, N,N-dibutylamino group, and N-acetyl-N-benzoylamino group. Furthermore, the above-mentioned groups may optionally be substituted by an alkyl group (e.g., methyl or ethyl), carboxyl group, sulfonic group, substituted (e.g., methyl or ethyl) or unsubstituted carbamoyl group, substituted (e.g., methyl or ethyl) or unsubstituted sulfamoyl group, or halogen atom (e.g., chlorine or bromine), or combinations thereof; examples thereof include 6-carboxy-1,2,3-benzotriazol-1-yl group, 6-sulfo-1,2,3-benzotriazol-1-yl group, 5-chloro-1,2,3-benzotriazol-1-yl group, 4-carboxyphthalimide group, 4-aminophthalimide group, sulfosuccinimide group and aspargine group.

Examples of compounds of the formula (I) which can be used according to this invention are described below. However, the invention is not intended to be construed as being limited to these examples.

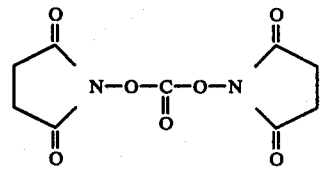
Compound (1)

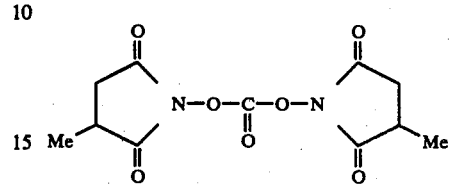
Compound (2)

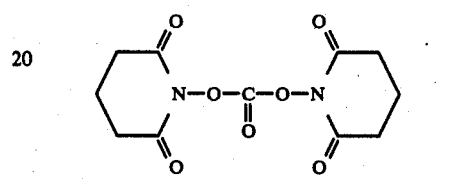
Compound (3)

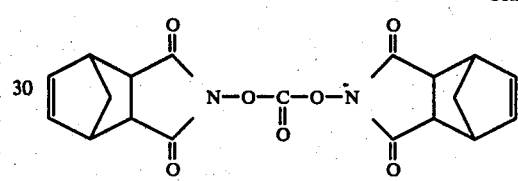
Compound (4)

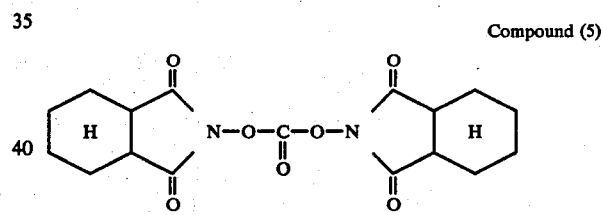
Compound (5)

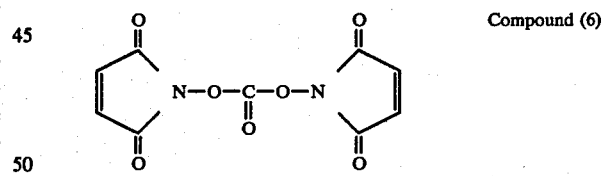
Compound (6)

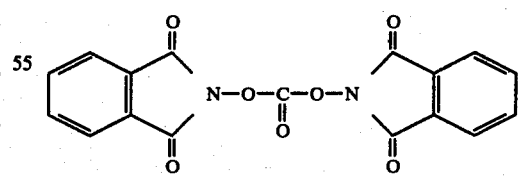
Compound (7)

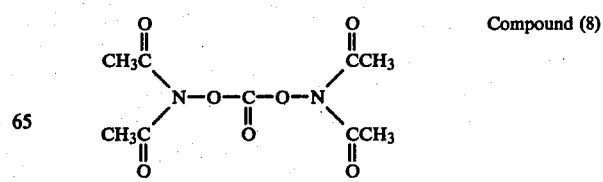
Compound (8)

-continued

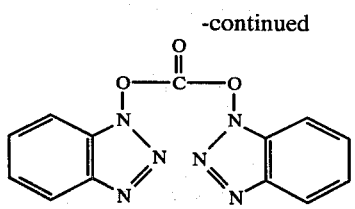
Compound (9)

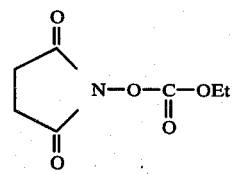
Compound (10)

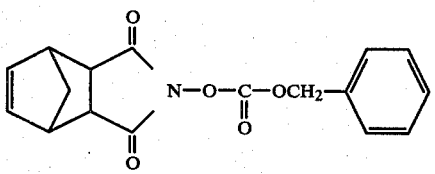
Compound (11)

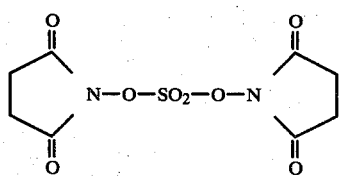
Compound (12)

The compounds used in this invention can be divided into two groups according to the method of synthesis. The compounds wherein n is 2 can be synthesized by treating the corresponding N-hydroxy compound with trimethylsilyl diethylamine to form a silyl compound, which is then reacted with phosgene to form the compound. Alternatively, the N-hydroxy compound may be directly reacted with phosgene. The hardener compounds wherein n is 1 can be synthesized by reacting the corresponding N-hydroxy compound with an acid halide in the presence of triethylamine. In this case, triethylamine may be replaced by a tertiary amine.

Examples of synthesis of the compounds that can be used in this invention are described below.

SYNTHESIS EXAMPLE 1

Synthesis of Compound (1)

A mixture of 15 g (0.1 mol) of N-hydroxysuccinimide and 14.5 g (0.1 mol) of trimethylsilyl diethylamine (TMS-DEA) serving as a silyl-introducing agent was heated under reflux for 2 hours. After distilling off the unreacted TMS-DEA, tetrahydrofuran (THF) was added, followed by addition of phosgene while cooling externally with ice. After 5 hours of stirring, the excess phosgene and THF were distilled off. When the crystals obtained by washing the residue with acetone were recrystallized from acetonitrile, 10.1 g of colorless crystals of Compound (1) were produced in a yield of 80%. Melting point: 211° C. to 215° C.

| | Elemental Analysis | | |
|---|---|---|---|
| | C | H | N |
| Calcd. (%) | 42.20 | 3.14 | 10.93 |
| Found (%) | 42.15 | 3.13 | 10.74 |

SYNTHESIS EXAMPLE 2

Synthesis of Compound (4)

The procedure of Synthesis Example 1 was repeated, except that the N-hydroxysuccinimide was replaced by N-hydroxy-5-norbornene-2,3-dicarboxyimide. Colorless crystals of N,N'-bis(5-norbornene-2,3-dicarboxyimidyl) carbonate were produced. Melting point: 242° C. to 245° C. (with decomposition).

| | Elemental Analysis | | |
|---|---|---|---|
| | C | H | N |
| Calcd. (%) | 57.97 | 2.29 | 7.95 |
| Found (%) | 57.97 | 2.35 | 8.10 |

SYNTHESIS EXAMPLE 3

Synthesis of Compound (7)

The procedure of Synthesis Example 1 was repeated, except that the N-hydroxysuccinimide was replaced by N-hydroxyphthalimide. Colorless crystals of N,N'-diphthalimidylcarbonate were produced. Melting point: 208° C. to 210° C.

| | Elemental Analysis | | |
|---|---|---|---|
| | C | H | N |
| Calcd. (%) | 59.38 | 4.20 | 7.29 |
| Found (%) | 59.11 | 4.14 | 7.29 |

SYNTHESIS EXAMPLE 4

Synthesis of Compound (10)

Twenty-three grams of N-hydroxysuccinimide was dissolved in 200 ml of dry dioxane. While the solution was held at room temperature, 19.1 ml of ethyl chloroformate and 27.8 ml of triethylamine were added dropwise simultaneously. After the addition, the reaction mixture was stirred for 1 hour at room temperature. The resulting hydrochloride of triethylamine was removed by filtration, and the filtrate was concentrated. The residue was dissolved in 200 ml of chloroform, washed with cold water, dried with anhydrous sodium sulfate, and concentrated under vacuum to provide 26 g of white acicular crystals of Compound (10) in a yield of 69%. Melting point: 52° C. to 53° C.

| | Elemental Analysis | | |
|---|---|---|---|
| | C | H | N |
| Calcd. (%) | 44.92 | 4.85 | 7.48 |
| Found (%) | 44.75 | 4.79 | 7.68 |

SYNTHESIS EXAMPLE 5

Synthesis of Compound (11)

This compound was produced form N-hydroxysuccinimide and benzyl chloroformate according to the method described in Japanese Patent Application (OPI) No. 1459/76 (the term "OPI" as used herein refers to a "published unexamined Japanese patent application"). (This Japanese Patent Application (OPI) No. 1459/76 is related to a synthesis method of N-hydroxylmaleimide and describes the Compound (11) of this invention as an intermediate.) The compound had a melting point of 142° C. to 143° C. (documented value in the Japanese Patent Application (OPI) No. 1459/76: 140°–141° C.).

|  | Elemental Analysis | | |
|---|---|---|---|
|  | C | H | N |
| Calcd. (%) | 60.95 | 4.16 | 4.44 |
| Found (%) | 61.00 | 4.20 | 4.38 |

When these compounds were incorporated in a gelatin-containing photographic layer as a hardener, only slight undesirable effects (such as impaired photographic characteristics (increased fogging and reduced sensitivity), stain formation, and reaction with a coupler contained in the color photographic light-sensitive material) were observed. The gelatin hardened so rapidly that the final degree of hardening was reached within a few days after application and no substantial post-hardening (i.e., a further increase in the degree of hardening) was observed.

These compounds have a high affinity for water and required no special organic solvent for incorporation in a gelatin layer. This eliminates unwanted effects such as uneven application due to the use of such organic solvent. Additionally, these compounds can be used without providing protection against potential hazards such as explosions. Because of the absence of any severe physiological effects and low vapor pressure, these compounds present very little risk to the human body.

These advantages of the compounds used in this invention probably result from the substantial absence of low-polarity groups in their structure. Perhaps because of this characteristic, the compounds are substantially free from lypophilic moieties that would let them be absorbed by lipids which would render them toxic to human beings. The absence of lypophilic moieties perhaps also results in increased affinity for water and explains the fact that the compounds are water-soluble.

The gelatin hardening method according to this invention can be carried out in a conventional gelatin hardening method for gelatin-containing layers of photographic light-sensitive materials as described, for example, in U.S. Pat. Nos. 4,124,397, 4,013,460, 3,481,190, 3,832,181 and 3,840,370.

The amount of hardening agent used according to the present invention when such is incorporated in a gelatin layer of a photographic material can be suitably chosen depending on the purpose. Generally, a suitable amount ranges from about 0.1% to about 20% by weight, based on the weight of dry gelatin. A most preferred amount ranges from 0.5% to 10% by weight. If the amount of the hardening agent of this invention is above about 20% by weight based on the dry gelatin, it becomes impossible to form films from the aqueous solution of gelatin by, for example, coating or spray coating, because the aqueous solution of gelatin sometimes gelatinizes and hardens. On the other hand, if the amount is below about 0.1% by weight, although formation of the films can be carried out using the aqueous solution of gelatin, the resulting films do not sufficiently harden after drying, and the strength of such films is insufficient. On the contrary, when the amount of the hardening agent is within the above-described range, the property of rapid hardening of the gelatin, which is a characteristic of the present invention, is appropriately exhibited.

The hardening agent according to the present invention can be used individually, or two or more hardening agents according to the present invention may be used as a mixture thereof.

Furthermore, hardening agents according to this invention can be used together with other known hardening agents. Examples of known hardening agents with which the hardening agent can be used include, for example, aldehyde compounds, such as formaldehyde or glutaraldehyde, ketone compounds, such as diacetyl or cyclopentanedione, bis(2-chloroethylurea), 2-hydroxy-4,6-dichloro-1,3,5-triazine, reactive halogen-containing compounds as described in U.S. Pat. Nos. 3,288,775 and 2,732,303 and British Pat. Nos. 974,723 and 1,167,207, etc., divinylsulfone, 5-acetyl-1,3-diacryloylhexahydro-1,3,5-triazine, reactive olefinic compounds as described in U.S. Pat. Nos. 3,635,718 and 3,232,763 and British Pat. No. 994,869, N-hydroxymethylphthalimide, N-methylol compounds as described in U.S. Pat. Nos. 2,732,316 and 2,386,168, isocyanates as described in U.S. Pat. No. 3,103,437, aziridine compounds as described in U.S. Pat. Nos. 3,017,280 and 2,983,611, acid derivatives as described in U.S. Pat. Nos. 2,725,294 and 2,725,295, carbodiimide compounds as described in U.S. Pat. No. 3,100,704, epoxy compounds as described in U.S. Pat. No. 3,091,537, isoxazole compounds as described in U.S. Pat. Nos. 3,321,313 and 3,543,292, halocarboxyaldehydes, such as mucochloric acid, dioxane derivatives, such as dihydroxydioxane or dichlorodioxane, and inorganic hardening agents, such as chromium alum or zirconium sulfate, etc. Further, the hardening agents used in this invention can be used together with precursor type compounds, such as alkali metal bisulfite-aldehyde addition products, methylol derivatives of hydantoin or monohydric aliphatic nitroalcohols, etc. When the hardening agent of the present invention is used together with other hardening agent(s), the ratio thereof can be appropriately chosen depending on the particular effect desired, but it is preferred to use hardening agent(s) according to the present invention in an amount of at least 50 mol% of the total amount of hardening agents.

If the hardener of this invention is used in a photographic light-sensitive material, a silver halide emulsion is used that is generally prepared by mixing solution of a water-soluble silver salt (such as silver nitrate) and a solution of a water-soluble halide salt (e.g., potassium bromide) in the presence of a solution of water-soluble polymer such as gelatin. Examples of the silver halide include not only silver chloride and silver bromide but also mixed silver halides such as silver chlorobromide, silver iodobromide and silver chloroiodobromide. Particles of these silver halides may be cubic, octahedral, or mixed crystal structures. There is no particular limitation on the particle size and average particle size distribution, and any generally suitable values can be selected.

These photographic emulsions are described in various publications such as Mees, *The Theory of Photographic Process*, 4th Ed., Macmillan Publishing Co., (1977) and P. Glafikides, *Chimie Photographique*, Paul Montel, (1957), and they can be prepared by generally known methods such as ammoniacal methods, neutral methods, and acid methods.

These silver halide emulsions may be subjected to conventional chemical sensitization. Useful chemical sensitizers include gold compounds such as chloroaurate and gold trichloride of the type taught in U.S. Pat. Nos. 2,399,083, 2,540,085, 2,597,856 and 2,597,915; salts of noble metals such as platinum, palladium, iridium, rhodium and ruthenium as described in U.S. Pat. Nos. 2,448,060, 2,540,086, 2,566,245, 2,566,263 and 2,598,079; sulfur compounds that react with silver salts to form silver sulfide as described in U.S. Pat. Nos. 1,574,944, 2,410,689, 3,189,458 and 3,501,313; stannous salts of the type described in U.S. Pat. Nos. 2,487,850, 2,518,698, 2,521,925, 2,521,926, 2,694,637, 2,983,610, and 3,201,254; amines and other reducing substances.

If desired, the photographic emulsions using the hardener of this invention may be subjected to spectral sensitization or supersensitization with cyanine dyes such as cyanine, merocyanine, and carbocyanine dyes, which may be used independently, as mixtures thereof, or in admixture with a styryl dye.

For the purpose of preventing a reduction in sensitivity and an occurrence of fog during preparation of the light-sensitive materials, during storage or during processing of the light-sensitive materials, various kinds of compounds may be added to the above-described photographic emulsions. Many known compounds, for example, heterocyclic compounds, mercury containing compounds, mercapto compounds, metal salts as well as 4-hydroxy-6-methyl-1,3,3a,7-tetrazaindene, 3-methylbenzothiazole and 1-phenyl-5-mercaptotetrazole can be used for such purposes.

Examples of suitable compounds capable of achieving the above are described in C. E. K. Mees and T. H. James, *The Theory of the Photographic Process*, 3rd Ed., pp. 344–349, Macmillan Co., New York (1966) and in the following patents: U.S. Pat. Nos. 1,758,576, 2,110,178, 2,131,038, 2,173,628, 2,697,040, 2,304,962, 2,324,123, 2,394,198, 2,444,605~8, 2,566,245, 2,694,716, 2,697,099, 2,708,162, 2,728,663~5, 2,476,536, 2,824,001, 2,843,491, 2,886,437, 3,052,544, 3,137,577, 3,220,839, 3,226,231, 3,236,652, 3,251,691, 3,252,799, 3,287,135, 3,326,681, 3,420,688 and 3,622,339 and British Pat. Nos, 893,428, 403,789, 1,173,609 and 1,200,188.

The gelatin to which the hardening agent of the present invention can be applied includes the so-called alkali treated (lime treated) gelatin which is prepared by treatment in an alkali bath when the gelatin is extracted from collagen, acid treated gelatin which is prepared by treatment in an acid bath and enzyme treated gelatin as described in *Bull. Soc. Sci. Photo. Japan*, No. 16, p. 30 (1966). Further, hardening agent according to the present invention can be applied to gelatin having a low molecular weight which is prepared by partially hydrolyzing the gelatin in a water bath with heating or by reacting with a protease.

The gelatin to which the hardening agent of the present invention can be applied may be partially replaced, if desired, by colloidal albumin, casein, cellulose derivatives, such as carboxymethyl cellulose or hydroxyethyl cellulose, etc., saccharose derivatives such as agar, sodium alginate or starch derivatives, etc., or synthetic hydrophilic colloids, such as polyvinyl alcohol, poly-N-vinylpyrrolidine, acrylic acid copolymers, polyacrylamide or derivatives thereof or partially hydrolyzed products thereof, and also replaced by the so-called gelatin derivatives, namely, those wherein the amino groups, imino groups, hydroxy groups or carboxyl groups as functional groups in the gelatin molecule are reacted with reactants having a group capable of reacting with such groups or graft polymers prepared by grafting the molecular chain of other high molecular weight materials thereto.

Examples of suitable reactants for producing the above-described gelatin derivatives include isocyanates, acid chlorides and acid anhydrides as described in U.S. Pat. No. 2,614,928, acid anhydrides as described in U.S. Pat. No. 3,118,766, bromoacetic acids as described in Japanese Patent Publication No. 5514/64, phenyl glycidyl ethers as described in Japanese Patent Publication No. 26845/67, vinyl sulfone compounds as described in U.S. Pat. No. 3,132,945, N-allyl vinylsulfonamides as described in British Pat. No. 861,414, maleinimide compounds as described in U.S. Pat. No. 3,186,846, acrylonitriles as described in U.S. Pat. No. 2,594,283, polyalkylene oxides as described in U.S. Pat. No. 3,312,553, epoxy compounds as described in Japanese Patent Publication No. 26845/67, acid esters as described in U.S. Pat. No. 2,763,639 and alkane sultones as described in British Pat. No. 1,033,189.

Branched polymeric materials suitable for grafting to gelatin appear in U.S. Pat. Nos. 2,763,625, 2,831,767 and 2,956,884, *Polymer Letters*, Vol. 5, p. 595, (1967), *Phot. Sci. Eng.*, Vol. 9, p. 148 (1965) and *J. Polymer Sci.*, A-1, Vol. 9, p. 3199 (1971). Polymers and copolymers of the so-called vinyl monomers such as acrylic acid, methacrylic acid or the esters, amides or nitriles thereof, or styrene, etc., can be used as such materials. However, hydrophilic vinyl polymers having a relatively high degree of compatibility with gelatin, such as polymers and copolymers of acrylic acid, acrylamide, methacrylamide, hydroxyalkyl acrylates or hydroxyalkyl methacrylates, etc., are particularly preferred.

In using the hardening agent of the present invention for photographic light-sensitive materials, synthetic polymer compounds, such as a latex of water-dispersable vinyl polymers, and particularly compounds which increase the dimensional stability of the photographic materials, may be incorporated directly into photographic emulsion layers or other photographic layers individually or as a mixture (of different kinds of polymers), or may be incorporated together with hydrophilic water-permeable colloids. Examples of such polymers include many kinds, as described, for example, in U.S. Pat. Nos. 2,376,005, 2,739,137, 2,853,457, 3,062,674, 3,411,911, 3,488,708, 3,525,620, 3,635,715, 3,607,290, and 3,645,740 and British Pat. Nos. 1,186,699 and 1,307,373. Of these compounds, copolymers and homopolymers of alkyl acrylates, alkyl methacrylates, acrylic acid, methacrylic acid, sulfoalkyl acrylates, sulfoalkyl methacrylates, glycidyl arylate, glycidyl methacrylate, hydroxyalkyl acrylates, hydroxyalkyl methacrylates, alkoxyalkyl acrylates, alkoxyalkyl methacrylates, styrene, butadiene, vinyl chloride, vinylidene chloride, maleic acid anhydride and itaconic acid anhydride are generally used. If desired, the so-called graft type emulsion polymerization latexes which were prepared by emulsion polymerization of the above-described vinyl compounds in the presence of hydrophilic protective colloid high molecular materials may be used.

In using the gelatin hardening agent of the present invention for photographic light-sensitive materials, matting agents can be used together therewith. Examples of suitable matting agents are finely divided particles of water-insoluble organic or inorganic compounds having an average particle size of from about $0.2\mu$ to $10\mu$, and preferably from $0.3\mu$ to $5\mu$. Examples of organic compounds preferably used include water-dispersible vinyl polymers, such as polymethyl acrylate, polymethyl methacrylate, polyacrylonitrile, acrylonitrile-α-methylstyrene copolymers, polystyrene, styrene-divinylbenzene copolymers. Examples of inorganic compounds which are preferably used include silicon dioxide, titanium dioxide, magnesium dioxide, aluminum dioxide, barium sulfate.

In using the gelatin hardening agent of the present invention for photographic light-sensitive materials, couplers may be also used in combination therewith. In such cases, the so-called non-diffusible couplers are incorporated in silver halide emulsion layers. Examples of couplers which can be used are 4-equivalent diketomethylene type yellow couplers and 2-equivalent diketomethylene type yellow couplers, such as the compounds described in U.S. Pat. Nos. 3,415,652, 3,447,928, 3,311,476 and 3,408,194, etc., the compounds described in U.S. Pat. Nos. 2,875,057, 3,265,506, 3,409,439, 3,551,155, and 3,551,156, etc., and the compounds described in Japanese Patent Application (OPI) Nos. 26133/72 and 66836/73, etc.; 4-equivalent and 2-equivalent pyrazolone type magenta couplers and imidazolone type magenta couplers, such as the compounds described in U.S. Pat. Nos. 2,600,788, 2,983,608, 3,062,653, 3,214,437, 3,253,924, 3,419,391, 3,419,808, 3,476,560 and 3,582,322, Japanese Patent Publication No. 20636/70 and Japanese Patent Application (OPI) No. 26133/72; and α-naphthol type cyan couplers and phenol type cyan couplers, such as the compounds described in U.S. Pat. Nos. 2,474,293, 2,698,794, 3,034,892, 3,214,437, 3,253,924, 3,311,476, 3,458,315 and 3,591,383 and Japanese Patent Publication Nos. 11304/67 and 32461/69. In addition, the compounds described in U.S. Pat. Nos. 3,227,554, 3,297,445, 3,253,924, 3,311,476, 3,379,529, 3,516,831, 3,617,291 and 3,705,801 and German Patent Application (OLS) No. 2,163,811 may be used.

Surface active agents may also be added, either individually or as a mixture thereof, to the photographic emulsions of the photographic light-sensitive materials to which the hardening agent of the present invention is applied. Although surface active agents are generally used as coating assistants, they are sometimes used for other purposes, such as emulsification, sensitization, improvement of photographic properties, prevention of electrostatic charging or prevention of adhesion, and so forth.

These surface active agents can be classified into natural surface active agents, such as saponin, nonionic surface active agents, such as alkylene oxide type, glycerin type, and glycidol type agents, etc., cationic surface active agents, such as higher alkylamines, quaternary ammonium salts, pyridine and other heterocyclic compounds, phosphonium or sulfonium compounds, etc., anionic surface active agents which contain acid groups, such as carboxylic acid, sulfonic acid, phosphoric acid, sulfuric acid ester or phosphoric acid ester groups, etc., and amphoteric surface active agents, such as amino acids, aminosulfonic acids, sulfuric acid esters, and phosphoric acid esters of aminoalcohols.

Examples of such useful surfactants are described in U.S. Pat. Nos. 2,271,623, 2,240,472, 2,288,226, 2,739,891, 3,068,101, 3,158,484, 3,201,253, 3,210,191, 3,294,540, 3,415,649, 3,441,413, 3,442,654, 3,475,174, 3,545,974, German Patent Application (OLS) No. 1,942,665, British Pat. Nos. 1,077,317 and 1,198,450, and publications such as Oda Ryohei et al., *Kaimen Kasseizai no Gosei to Sono Oyo (Synthesis of Surfactants and its Applications)*, Maki Shoten, (1964), A. W. Perry, *Surface Active Agents*, Interscience Publication Incorporated, (1958), and J. P. Sisley, *Encyclopedia of Surface Active Agents*, Vol. 2, Chemical Publishing Company, (1964).

The photographic emulsions described so far are coated on planar materials that will not undergo substantial dimensional changes during processing, and such materials may be suitably selected from among rigid supports such as glass, metal or ceramic or flexible supports.

Examples of typical flexible supports include cellulose acetate films, polyethylene terephthalate films, polycarbonate films, laminated films of the above-described films, baryta coated paper, paper laminated or coated with α-olefin polymers and, particularly, with polymers of an α-olefin having from 2 to 10 carbon atoms, which have been conventionally used for photographic light-sensitive materials.

In using a hardening agent according to the present invention, the layers of the photographic light-sensitive materials can be formed by various coating methods, such as dip coating, air-knife coating, curtain coating, spray coating or extrusion coating using a hopper such as is described in U.S. Pat. No. 2,681,294.

If desired, two or more layers can be coated at the same time using methods such as those described in U.S. Pat. Nos. 2,761,791, 3,508,947, 2,941,898 and 3,526,528, etc.

The gelatin hardening method of this invention can be used with advantage not only for photographic light-sensitive materials, but also in all industries that use hardened gelatin. For example, the method of this invention can be used for hardening a microcapsule of the type described in U.S. Pat. No. 4,016,098. More particularly, such microcapsules can be hardened in the following manner: a gelatin membrane formed by coacervation is gelled by cooling, and hardened in the presence of a gelatin hardener or by rendering the system pH alkaline with an alkali (e.g., NaOH) added in the presence of a gelatin hardener. Further according to the method of this invention, the hardening rate can be accelerated by using the compound of the formula (I) of this invention in addition to a conventional gelatin hardener.

In hardening a microcapsule, gelatin and the compound of the formula (I) of this invention can be used in the same ratio as specified above for photographic light-sensitive materials.

The method of this invention is now described in greater detail by reference to the following examples which are given here for illustrative purposes only and are by no means intended to limit the scope of the invention.

EXAMPLE 1

To a 7 wt% gelatin solution, the compounds indicated in Table 1 were added in the amounts also shown in Table 1. Each of the mixtures was applied uniformly to a subbed polyethylene terephthalate support and dried to form a gelatin layer having a dry thickness of about 7μ. The resulting samples were stored in an incubator at 25° C. under 55% RH for 14 days. On the first day, seventh day and fourteenth day of the storage, part of each sample was recovered from the incubator and its degree of swelling in water (25° C.) was measured. The degree of swelling (Q) is represented by the following formula:

$$Q = \frac{\text{thickness of swollen membrane}}{\text{thickness of dry membrane}}$$

The scratch resistance of each sample was determined as follows: each sample was immersed in water and, a stylus having a steel ball (radius: 0.4 mm) on the tip was pressed against the surface of the sample and moved parallel with the surface at a rate of 2.5 mm per second under a load that varied continuously from 0 to 200 g. The load that caused a scratch to develop on the gelatin layer was measured. The results of measurement of the degree of swelling and scratch resistance are shown in Table 1 below in which Compound (A) represents a sodium salt of 2,4-dichloro-6-hydroxy-S-triazine.

As is clear from the table, the compounds of this invention are water-soluble and achieve very quick hardening of gelatin so that a predetermined degree of hardening is reached within a few days of application of gelatin.

TABLE 1

| Compound | Amount Added (per 100 g of gelatin) | Q 1 Day | Q 7 Days | Q 14 Days | Scratch Resistance (7 days after application) (g) |
|---|---|---|---|---|---|
| Control | 0 | 10.1 | 10.0 | 10.2 | 7 |
| Compound (1) | 6.4 g (25 mmol) | 3.6 | 3.5 | 3.5 | 81 |
| Compound (3) | 7.1 g (25 mmol) | 4.0 | 3.6 | 3.5 | 79 |
| Compound (A) | 0.9 g (5 mmol) | 8.5 | 5.0 | 3.4 | 72 |

EXAMPLE 2

A photographic emulsion for high-sensitivity negative film was prepared by the conventional method and it contained 120 g of gelatin and 65 g of silver iodobromide per kg of the emulsion. To the emulsion, the compounds of this invention indicated in Table 2 were added in the amounts also shown in Table 2. Each of the mixtures was applied uniformly to a subbed triacetyl cellulose support and dried to form a gelatin layer having a dry thickness of 10μ. The resulting samples were stored at room temperature for 7 days, and their degree of swelling in water at 25° C. was measured in the same manner as described in Example 1. The film samples were exposed through an optical wedge, developed with a D-76 developer at 20° C. for 8 minutes, fixed, washed, dried and subjected to sensitometry for determination of their sensitivity and degree of fogging. The results are indicated in Table 2.

Table 2 clearly shows that the compounds of this invention provided a gelatin layer with satisfactory strength without impairing the photographic characteristics of the film product.

TABLE 2

| Compound | Amount Added (per 100 g of gelatin) | Photographic Characteristics 7 Days after Application Relative Sensitivity | Fog | Accelerated Conditions at 50° C. for 2 Days Relative Sensitivity | Fog | Membrane Strength Q (7 days after application) | Scratch Resistance (7 days after application) (g) |
|---|---|---|---|---|---|---|---|
| Control | 0 | 100 | 0.05 | 100 | 0.10 | 9.8 | 7 |
| Compound (1) | 6.4 g (25 mmol) | 93 | 0.05 | 92 | 0.06 | 3.4 | 83 |
| Compound (3) | 7.1 g (25 mmol) | 94 | 0.05 | 93 | 0.07 | 3.5 | 82 |
| Compound (A) | 0.9 g (5 mmol) | 88 | 0.04 | 87 | 0.05 | 4.9 | 74 |

EXAMPLE 3

A silver iodobromide emulsion containing 3.0 mol% of silver iodide was after-ripened in the presence of sodium thiosulfate and gold salt to provide maximum sensitivity. The resulting high-sensitivity negative emulsion was mixed with an O/W coupler emulsion (i.e., coupler emulsion which is dispersed as oil-in-water type dispersion) comprising a solution of 1-(2',4',6'-trichlorophenyl)-3-[3''-(2''',4'''-di-t-amylphenoxyacetamido)benzamido]-5-pyrazolone in a mixture of dibutyl phthalate and tricresyl phosphate that was dispersed in a gelatin solution using a mixture of sorbitan monolaurate, sulfonated oil and sodium dodecylbenzenesulfonate as an emulsifier. To the mixed emulsion, 6.4 g (25 mmol) of Compound (1) of this invention was added per 100 g of dry gelatin, and the mixture was applied to a subbed triacetyl cellulose base and dried to form a gelatin layer having a dry thickness of about 10μ. The resulting experimental color film having a single magenta layer was exposed through an optical wedge and color-developed with a developing agent comprising 4-amino-3-methyl-N-ethyl-β-hydroxyethylaniline sesquisulfate monohydrate. Sensitometry of the developed film showed that the compound of this invention did not impair the color developing function of the coupler, nor did it form a color stain.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising at least one gelatin-containing layer hardened by a hardening agent of the formula (I)

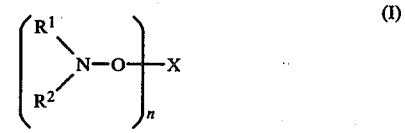

wherein

R¹ and R² each represent a monovalent group including a carbon atom or a nitrogen atom forming a bond together with the nitrogen atom N in the formula (I), the total number of carbon atoms in said monovalent groups being 4 or 5 carbon atoms; or $R^1$ and $R^2$ together form a heterocyclic ring which can contain an oxygen atom together with said nitrogen atom N, and n is 1 or 2; and when n is 1, X is

and Y is an alkyl group, having from 1 to 8 carbon atoms, an aryl group having from 6 to 12 carbon atoms or an aralkyl group having from 7 to 13 carbon atoms; and when n is 2, X is

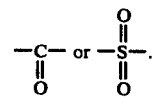

2. A silver halide photographic light-sensitive material as in claim 1 wherein $R^1$ or $R^2$ together form a 5- or 6-membered heterocyclic ring together with said nitrogen atom N.

3. A silver halide photographic light-sensitive material as in claim 1 or 2, wherein n is 2.

4. A silver halide photographic light-sensitive material as in claim 1, or 2, wherein n is 1.

5. A silver halide photographic light-sensitive material as in claim 1 wherein the hardening agent of the formula (I) is used in an amount of from about 0.1% to about 20% by weight based on the weight of dry gelatin.

* * * * *